(12) United States Patent
Jerome et al.

(10) Patent No.: US 6,696,584 B2
(45) Date of Patent: Feb. 24, 2004

(54) ISOMER ENRICHED CONJUGATED LINOLEIC ACID COMPOSITIONS

(75) Inventors: Daria Jerome, Owatonna, MN (US); Carl Skarie, Detroit Lakes, MN (US)

(73) Assignee: Natural ASA (NO)

( * ) Notice: Subject to any disclaimer, the term of this patent is extended or adjusted under 35 U.S.C. 154(b) by 146 days.

(21) Appl. No.: 10/023,598

(22) Filed: Dec. 18, 2001

(65) Prior Publication Data

US 2002/0082436 A1 Jun. 27, 2002

Related U.S. Application Data

(63) Continuation of application No. 09/789,583, filed on Feb. 22, 2001, which is a continuation of application No. 09/438,101, filed on Nov. 10, 1999, now Pat. No. 6,242,621, which is a continuation of application No. 09/072,422, filed on May 4, 1998, now Pat. No. 6,060,514.

(51) Int. Cl.[7] ............................................. C07C 57/00
(52) U.S. Cl. ....................... 554/224; 554/223; 554/227; 514/558; 514/560; 514/962; 424/648; 424/807; 424/451
(58) Field of Search .................. 584/223, 224, 584/227; 514/558, 560; 424/648, 807

(56) References Cited

U.S. PATENT DOCUMENTS

| | | | |
|---|---|---|---|
| 2,242,230 A | 5/1941 | Burr | 260/398 |
| 2,350,583 A | 6/1944 | Bradley | 260/195.6 |
| 3,162,658 A | 12/1964 | Baltes et al. | 260/405.6 |
| 3,278,567 A | 10/1966 | Rathjen et al. | 260/405.6 |
| 3,729,379 A | 4/1973 | Ernken | 195/30 |
| 4,164,505 A | 8/1979 | Krajca | 260/405.6 |
| 4,381,264 A | 4/1983 | Struve | 560/405.6 |
| 5,017,614 A | 5/1991 | Pariza et al. | 514/558 |
| 5,070,104 A | 12/1991 | Pariza et al. | 514/549 |
| 5,208,356 A | 5/1993 | Pariza et al. | 554/79 |
| 5,288,619 A | 2/1994 | Brown et al. | 435/134 |
| 5,428,072 A | 6/1995 | Cook et al. | 514/560 |
| 5,430,066 A | 7/1995 | Cook et al. | 514/558 |
| 5,468,887 A | 11/1995 | Gupta | 554/169 |
| 5,554,646 A | 9/1996 | Cook et al. | 514/560 |
| 5,585,400 A | 12/1996 | Cook et al. | 514/560 |
| 5,674,901 A | 10/1997 | Cook et al. | 246/452 |
| 5,725,873 A | 3/1998 | Cook et al. | 424/442 |
| 5,760,082 A | 6/1998 | Cook et al. | 514/560 |
| 5,760,083 A | 6/1998 | Cook et al. | 514/560 |
| 5,804,210 A | 9/1998 | Cook et al. | 424/440 |
| 5,814,663 A | 9/1998 | Cook et al. | 514/560 |
| 5,827,885 A | 10/1998 | Cook et al. | 514/558 |
| 5,851,572 A | 12/1998 | Cook et al. | 426/2 |
| 5,855,917 A | 1/1999 | Cook et al. | 424/502 |
| 5,856,149 A | 1/1999 | Pariza et al. | 435/134 |
| 5,885,594 A | 3/1999 | Nilsen et al. | 424/401 |
| 5,986,116 A | 11/1999 | Iwata et al. | 554/126 |

FOREIGN PATENT DOCUMENTS

| | | | |
|---|---|---|---|
| AU | 253031 | 7/1964 | |
| EP | 779033 | 6/1997 | A23D/9/00 |
| GB | 558881 | 10/1944 | |
| WO | WO 96/34855 | 11/1996 | C07D/209/28 |

(List continued on next page.)

OTHER PUBLICATIONS

Cowan, "Isomerization and Trans–Esterifration," *JAOCS* 72:492–99 (1950).

(List continued on next page.)

*Primary Examiner*—Deborah D. Carr
(74) *Attorney, Agent, or Firm*—Medlen & Carroll, LLP

(57) ABSTRACT

Compositions and methods of using conjugated linoleic acid preparations enriched for the t10,c12 and c9,t11 isomers are disclosed. It is found that preparations of conjugated linoleic acid containing a ratio of t10,c12 to c9,t11 of about greater than 1.2:1 are desirable for a wide variety of nutritional, therapeutic and pharmacologic uses.

9 Claims, 2 Drawing Sheets

FOREIGN PATENT DOCUMENTS

| WO | WO 96/38137 | 12/1996 | |
|---|---|---|---|
| WO | WO 97/18320 | 5/1997 | |
| WO | WO 97/37546 | 10/1997 | ............ A23D/9/05 |
| WO | WO 97/46118 | 12/1997 | ............ A23L/1/30 |
| WO | WO 97/46230 | 12/1997 | .......... A61K/31/20 |
| WO | WO 98/05318 | 2/1998 | .......... A61K/31/20 |
| WO | WO 98/05319 | 2/1998 | .......... A61K/31/20 |

OTHER PUBLICATIONS

Christie et al., "Isomers in Commercial Samples of Conjugated Linoleic Acid," JAOCS 74 (11):1231 (1997).

Kepler et al., J. Biol. Chem. 241:1350–54 (1966).

W. Parodi, J. Nutr. 127(6):1055–60 (1997).

Belury, "Conjugated Dienoic Linoleate: A Polyunsaturated Fatty Acid with Unique Chemoprotective Properties," Nut. Rev. 53(4):83–9 (1995).

Ha et al., Cancer Res., 50:1097 (1991).

Birt et al., Cancer Res., 52:2035–s (1992).

Ip, Am. J. Clin. Nutr. 66(6):1523s (1997).

Sehat et al., Lipids 33(2):217–21 (1998).

Jie, et al., "High–Resolution Nuclear Magnetic Resonance Spectroscopy –Amplification to Fatty Acids and Triacylglycerols," Lipids 32 (10): 1019–34 (1997).

Scholfield and Koritalis, "A Simple Method for Preparation of Methyl trans–10,cis–12 Octadecadienoate," JOACS 47(8):303 (1970).

Ron Udell, Information About Conjugated Linoleic Acid, published by Soft Gel Technologies Incorporated.

Sugano et al., "Conjugated Linoleic Acid Modulates Tissue Levels of Chemical Mediators and Immunoglobulins in Rats," Lipids, 33(5):521–27 (1998).

Matreya Catalog, 1997, pp. 33–34.

Selin CLA Product Literature, Jan. 1997.

Hudtwalcker & Co. AS Technical Data Sheet, exact publication date unknown.

Lipid Technology Newsletter, Peter J. Barnes, Ed., vol. 4, No. 5, pp. 85–86 (Oct., 1998).

Natural Lipids Ltd. AS Technical Data Sheet, Jan. 20, 1997.

Theil et al., "Conjugated Linoleic Acid Improves Performance and Body Composition in Swine," Iowa State University Midwest Animal Sciences Meeting, Abstract 127:61 (1998).

Quinn et al., "A Comparison of Modified Tall Oil and Conjugated Linoleic Acid on Growing–Finishing Pig Growth Performance and Catcass Characteristics," Kansas State University and Lonza, Inc., Midwest Animal Sciences Meeting, Abstract 128:61 (1998).

Dugan et al., "The Effect of Conjugated Linoleic Acid on Fat to Lean Repartitioning and Feed Conversion in Pigs," Canadian Journal of Animal Science 77:723–725 (1997).

Shantha et al., "Conjugated Linoleic Acid Concentrations in Processed Cheese Containing Hydrogen Donors, Iron and Dairy –Based Additives," Food Chemistry 47:257–261 (1993).

Bradley et al., "Alkali–Induced Isomerization of Drying Oils and Fatty Acids," Ing. Eng. Chem. 34(2):237–242 (1942).

Jie et al., "Synthesis and Nuclear Magnetic Resonance Properties of All Geometrical Isomers of Conjugated Linoleic Acids," Lipids 32(10):1041–1044 (1997).

Arcos et al., "Rapid Enzymatic Production of acylglycerols from conjugated linoleic acid and glycerol in the solvent–free system," Biotechnology Letters 20:617 (1998).

Holman et al., "Unusual Isomeric Polyunsaturated Fatty Acids in Liver Phospholipids of Rats Fed Hydrogenated Oil," PNAS 88:4830–34 (1991).

Radlove et al., "Catalytic Isomerization of Vegetable Oils," Ind. Eng. Chem. 38(10):997–1002 (1946).

Scbedio et al., "Linoleic Acid Isomers in Heat Treated Sunflower Oils," JAOCS 65(3):362–366 (1988).

Sebedio et al., "Metabolites of Conjugated Isomers of Linoleic Acid (CLA) in the Rat," Biochem. Biophys. Acta 1345–5–10 (1997).

Chin et al., "Dietary Sources of Conjugated Dienoic Isomers of Linoleic Acids, a Newly Recognized Class of Anticarcinogens," J. Food. Camp. Anal. 5:185–197 (1997).

Park et al., "Effect of Conjugated Linoleic Acid on Body Composition in Mice," Lipids 32(8):853–58 (1997).

Berdeau et al., "A Simply Method of Preparation of Methyl trans–10, cir–12–and cis–9, tranx–11–Octadecadienoates from Methyl Linolcate," JAOCS 75:1749–1755 (1998).

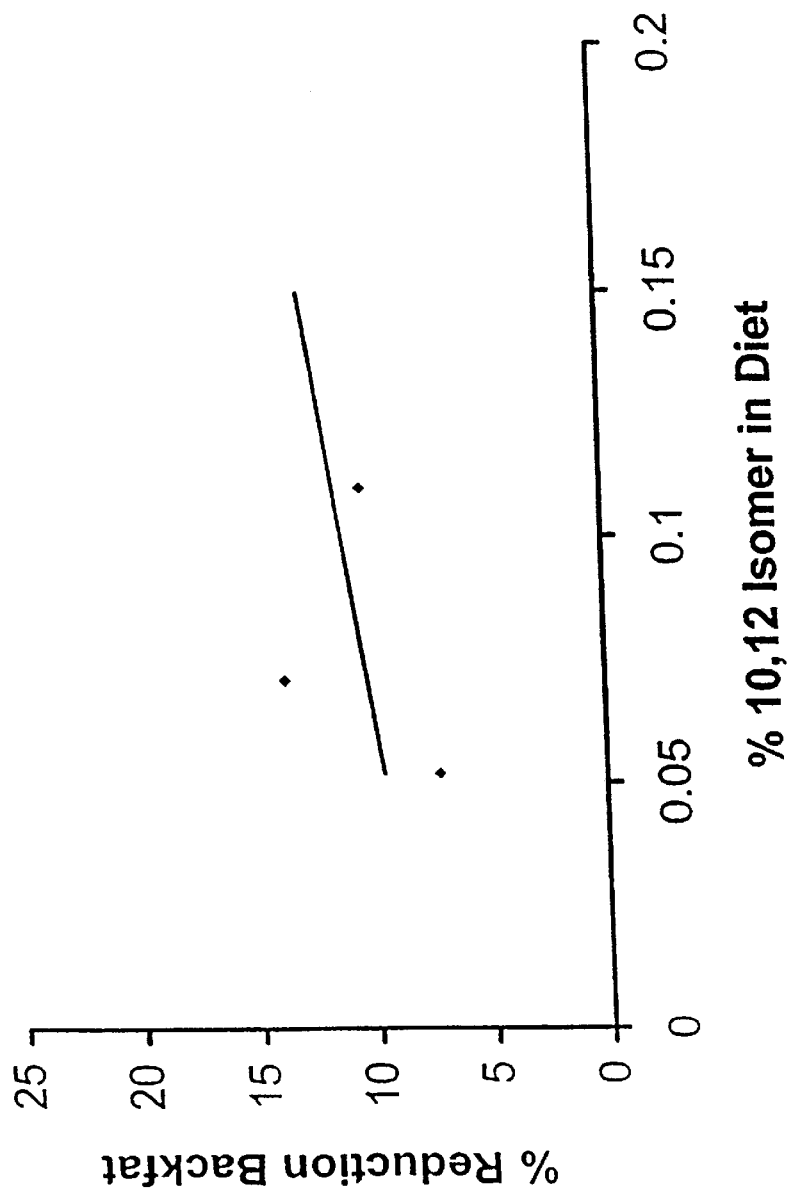

ISOMER ENRICHED CONJUGATED LINOLEIC ACID COMPOSITIONS

This application is a continuation of U.S. Ser. No. 09/789,583, filed Feb. 22, 2001 (allowed), which is a continuation of U.S. patent Ser. No. 09/438,101 filed on Nov. 10, 1999, now U.S. Pat. No. 6,242,621, which issued Jun. 5, 2001, 1999, which is a continuation of Ser. No. 09/072,422 filed on May 4, 1998, now U.S. Pat. No. 6,060,514, which issued on May 5, 2000.

FIELD OF THE INVENTION

The present invention relates to the field of human and animal nutrition, and in particular to compositions containing conjugated linoleic acids (CLA).

BACKGROUND OF THE INVENTION

Conjugated linoleic acid (CLA) has become the focus of numerous research programs which seek to capitalize on its nutritional, therapeutic, and pharmacologic properties.

The rearrangement of the double bonds of linoleic acid to conjugated positions has been shown to occur is during treatment with catalysts such as nickel or alkali at high temperatures, and during auto oxidation. Theoretically, eight possible geometric isomers of 9,11 and 10,12 octadecadienoic acid (c9,c11; c9,t11; t9,c11; t9,t11; c10,c12; c10,t12; t10,c12 and t10,t12) would form from the isomerization of c9,c12-octadecadienoic acid. A general mechanism for the isomerization of linoleic acid was described by J. C. Cowan in $JAOCS$ 72:492–99 (1950). It is believed that the double bond is polarized by the result of a collision with an activating catalyst. The polarized carbon atom and its adjoining carbon are then free to rotate and the forces are such as to make the deficient carbon atom essentially planar. When the system then moves to relieve these forces set up as a result of the collision, both cis and trans isomers are formed. The formation of certain isomers of CLA is thermodynamically favored. This is due to the co-planar characteristics of the five carbon atoms around the conjugated double bond and a spatial conflict of the resonance radical. The relatively higher distribution of 9,11 and 10,12 isomers apparently results from the further stabilization of the c9,t11 or t10,c12 geometric isomers.

Advances in gas chromatography have enabled researchers to precisely determine the isomer composition of samples of CLA. In Christie et al., $JAOCS$ 74 (11):1231 (1997), it was reported that the isomer distribution of a commercial sample of CLA was as follows: 8,10 (14%); 9,11 (30%); 10,12 (31%), and 11,13 (24%). In another study published by Christie et al appearing in $Lipids$ 33(2):217–21 (1998), the following CLA isomer composition of-a commercial CLA preparation was reported: t11,t13 (0.74%); t10,t12 (1.23%); t9,t11 (1.18%); t8,t10 (0.46%); c11,t13 and t11,c13 (21.7%) c10,t12 and t10,c12 (29.0%); c9,t11 and t9,c11 (29.5%); c8,t10 and t8,c10 (12.3%); c11,c13 (0.96%); c10,c12 (0.88%); c9,c11 (0.88%); and c8,c10 (0.20%). As can be seen from these studies, even though the formation of certain isomers are favored, other isomers of CLA can contribute greatly to the composition of alkali isomerized CLA preparations.

In 1978, researchers at the University of Wisconsin discovered the identity of a substance contained in cooked beef that appeared to inhibit mutagenesis. This substance was found to be CLA. Fatty acids with conjugated unsaturation are not normally constituents of the cow's diet. However, c9,t11 octadecadienoic acid is formed in the rumen as a first intermediate in the biohydrogenation of linoleic acid by linoleic acid isomerase from the anaerobic bacterium Butyrivibrio fibrisolvens as reported by Kepler et al., $J. Biol. Chem.$ 241:1350–54 (1966).

The biological activity of individual isomers of CLA has been the subject of some speculation. The literature generally suggests that the biologically active isomer is the c9,t11 isomer produced by Butyrivibrio fibrisolvens. For reviews adopting this position, see P. W. Parodi, $J. Nutr.$ 127(6):1055–60 (1997), M. A. Belury, $Nutrition Reviews$ 53(4):83–9 (1995). Further data supporting this assumption appears in Ha et al., $Cancer Res.,$ 50:1097 (1991). There, the researchers conducted labeled uptake studies which indicate that the 9,11 isomer appears to be somewhat preferentially taken up and incorporated into the phospholipid fraction of animal tissues, and to a lesser extent the 10,12 isomer.

The biological activity associated with CLA is diverse and complex. At present, very little is known about the mechanisms of action of CLA, although several preclinical and clinical studies in progress are likely to shed new light on the physiological and biochemical modes of action. The anticarcinogenic properties of CLA have been well-documented. Administration of CLA inhibits rat mammary tumorogenesis, as demonstrated by Ha et al., $Cancer Res.,$ 52:2035-s (1992). Ha et al., $Cancer Res.,$ 50:1097 (1990), reported similar results in a mouse forestomach neoplasia model. CLA has also been identified as a strong cytotoxic agent against target human melanoma, colorectal and breast cancer cells in vitro. A recent major review article confirms the conclusions drawn from individual studies. See Ip, $Am. J. Clin. Nutr.$ 66(6):1523s (1997).

Although the mechanisms of CLA action are still obscure, there is evidence that some component(s) of the immune system may be involved, at least in vivo. U.S. Pat. No. 5,585,400 (Cook, et al.) discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.) disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066 describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.) discloses a method utilizing CLA as a dietary supplement in which pigs, mice, and humans were fed diets containing 0.5 percent CLA. In each species a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al.) provided data showing that incorporation of CLA into animal feed (birds and mammals) increased the efficiency of feed conversion leading to greater weight gain in the CLA supplemented animals.

The potential beneficial effects of CLA supplementation for food animal growers is apparent. What is needed is a determination of what the actual biologically active isomers are and the appropriate ratios in which these isomers should be utilized.

SUMMARY OF THE INVENTION

The scientific literature suggests that the active CLA isomer is the c9,t11 isomer. However, as shown herein, an enhanced ratio of 10,12 to 9,11 isomers has a pronounced effect on the biological activity of CLA preparations. Therefore, it is an object of the present invention to provide compositions containing CLA isomers in biologically favorable ratios. It is also an object of the present invention to provide methods for using compositions containing CLA isomers in biologically favorable ratios, and of biologically active isomers in enriched content for optimization of the desired biological effects.

Accordingly, the present invention provides a conjugated linoleic acid composition comprising 10,12-linoleic acid and 9,11 linoleic acid, most preferably t10,c12 conjugated linoleic acid and c9,t11 conjugated linoleic acid, in a ratio of greater than 1.2:1, most preferably in a range of about 1.2:1 to 3:1. The conjugated linoleic acid composition provided may also be part a daily ration for a human or animal diet. The daily ration comprises a vehicle having a liquid component. The liquid component contains or comprises 0.01 to 10 gram equivalents of 10,12 conjugated linoleic acid, preferably t10,c12 conjugated linoleic acid. Alternatively, the invention provides a composition containing or comprising linoleic acid isomers, the isomers being characterized in containing or comprising a mixture of greater than 90 percent t10,c12 and c9,t11 CLA isomers. Preferably, the isomers are present in a ratio of about greater than 1:2:1 in favor of t10,c12.

The invention also provides a conjugated linoleic acid composition containing or comprising at least 50 percent conjugated linoleic acid isomers. The CLA isomers may be characterized as containing greater than 90 percent of a mixture of t10,c12 and c9,t11 isomers. Preferably the ratio of these isomers is greater than 1.2:1 in favor of the t10,c12 isomer.

The compositions of the present invention find a wide variety of nutritional, therapeutic and pharmacological uses. These uses include: the reduction of body fat in animals; increasing muscle mass in animals; increasing feed efficiency in animals, reducing body weight in humans, attenuating allergic reactions in animals; preventing weight loss due to immune stimulation in animals; elevating CD-4 and CD-8 cell counts in animals; increasing the mineral content of bone in animals; preventing skeletal abnormalities in animals; and, decreasing the amount of cholesterol in the blood of animals.

BRIEF DESCRIPTION OF THE DRAWINGS

FIG. 2 is a plot of a linear regression analysis of three separate studies comparing the total percentage of the 10,12 isomer of CLA in the diet of hogs to percent reduction backfat.

DESCRIPTION OF THE PREFERRED EMBODIMENT

Figure 1:
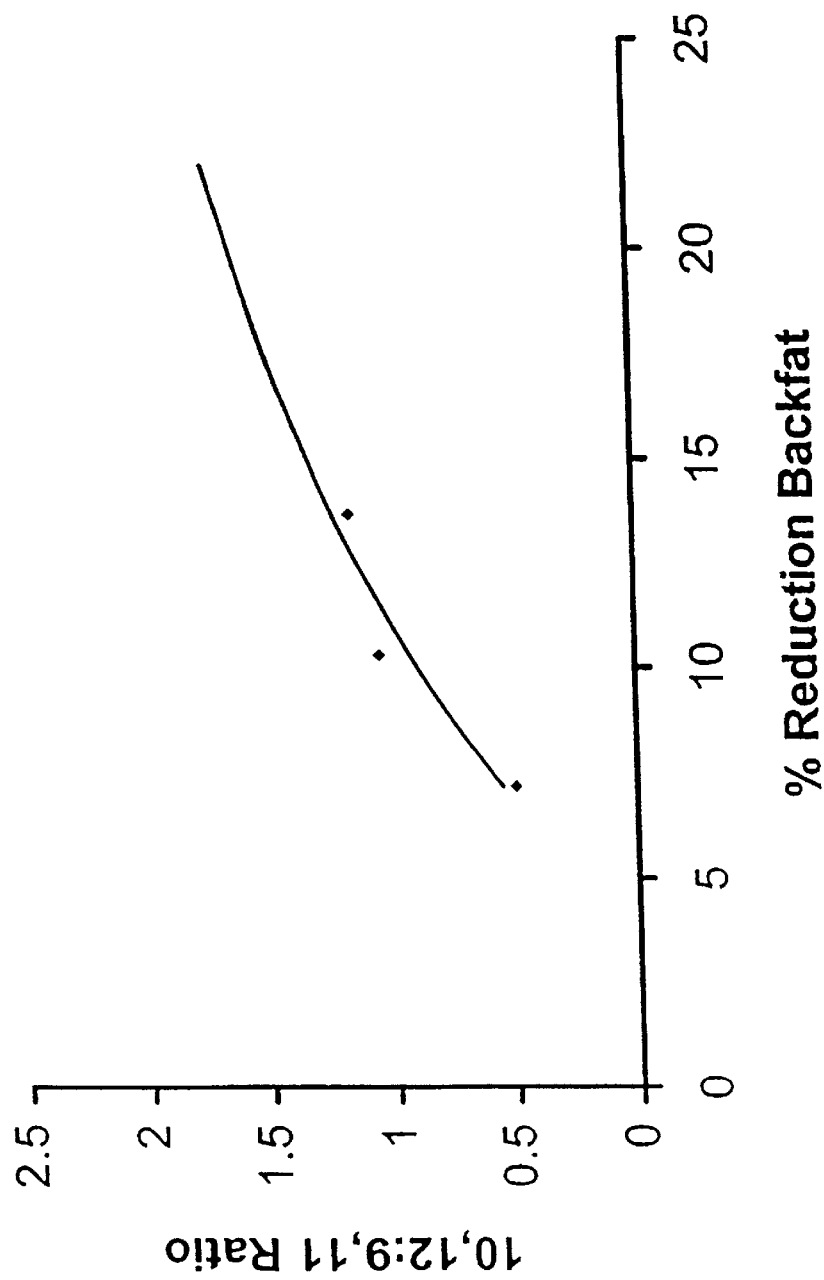
FIG. 1 is a plot of a logarithmic regression analysis of three separate studies comparing the ratio of the 10,12 and 9,11 isomers of CLA to percent reduction backfat in hogs.

Various uses of CLA have been well-documented in the patent and scientific literature. These uses may be divided into two general categories. The first category is the use of CLA nutritively as a dietary supplement. The second category is therapeutic and pharmacological uses.

U.S. Pat. No. 5,554,646 (Cook et al.), incorporated herein by reference, discloses the use of CLA for reducing body fat in animals. In this method, a safe and effective amount of CLA sufficient to cause reduction of body weight is fed to the animal. Mice fed a diet containing 0.5% CLA had a total fat content at the end of feeding that was significantly lower than the fat content of control mice fed a diet containing 0.5% corn oil. The exact amount of CLA to be administered to reduce body fat depends upon the animal, the form of CLA employed, and the route of administration. The amount generally ranges from about 0.001 g/kg to about 1 g/kg of the animal's body weight. Pharmaceutical amounts will generally range from about 1,000 parts per million (ppm) to about 10,000 ppm of CLA of the human's diet. However, the upper limit of the amount to be employed is not critical because CLA is relatively nontoxic. CLA for this and other uses may also be prepared in a variety of forms. These include nontoxic sodium or potassium salts of CLA in combination with a pharmaceutical diluent and active esters. CLA may also be incorporated directly into animal feed or food to be fed to a human so that CLA comprises approximately 0.01% to 2.0% or more by weight of the animal's or human's food. This patent also disclosed that supplementation of an animal's diet with CLA may serve to preserve body protein in an animal and to increase muscle protein in an animal.

Another nutritive use of CLA is disclosed in U.S. Pat. No. 5,428,072 (Cook et al.). There, feeding a safe and effective amount of CLA to animals is shown to enhance weight gain and feed efficiency in the animal. Groups of chicks fed a diet supplemented with 0.5% CLA demonstrated equivalent weight gain to control chicks fed 0.5% linoleic acid even though the CLA-fed chicks consumed less food. Furthermore, chicks fed 0.5% CLA and subsequently injected with endotoxin demonstrated weight gain, while chicks fed control diets either lost weight or gained very little weight. Similar results were seen in rats fed a diet containing 0.5% CLA and rabbits fed either 0.5% or 1% CLA. Guidelines for amounts of CLA to be fed or included in the diet are identical to those disclosed in U.S. Pat. No. 5,554,646.

Studies have also demonstrated that CLA may be used to actually reduce body weight in humans. In a double blind study conducted in Norway by Erling Thom in 1997, the diets of 20 healthy individuals were supplemented with either 3 gms of a CLA mixture or 3 gms of a placebo. The group fed CLA experienced both a decrease in body weight and body fat percentage while the group fed the placebo experienced an increase in body weight and body fat percentage. PCT Publication WO 97/46230 discloses a method for maintaining an existing level of body fat and/or body weight. The claims of that patent rely on an anecdotal, uncontrolled study wherein CLA was consumed by a total of 3 individuals.

Other patents on CLA use have focused on CLA's role in immune response. U.S. Pat. No. 5,585,400 (Cook et al.), herein incorporated by reference, discloses a method for attenuating allergic reactions in animals mediated by Type I or TgE hypersensitivity by administering a diet containing CLA. This patent also discloses administering CLA in concentrations of about 0.1 to 1.0% to preserve numbers of white blood cells. The studies disclosed in that patent utilized a guinea pig trachea allergy model Guinea pigs were fed 0.25% CLA or control diets for two weeks, then immunized with ovalbumin on weeks two and three for hyperimmunization. A superfusion model system was used to determine if feeding CLA had any effect on the allergen-induced tracheal contraction. Tracheae from guinea pigs fed CLA were more stable in the superfusion system than tracheae of control-fed guinea pigs. When allergen was infused over the guinea pig trachea, less traecheic contraction was observed in the tissue of the CLA-fed animals. The white blood cell count of animals fed CLA was elevated as compared to control animals, the CLA-fed animals having a white blood cell count of $3.5 \times 10^6 +/- 0.6$ as compared to $2.4 \times 10^6 +/- 0.3$ for the control animals.

The use of CLA to enhance growth and prevent anorexia and weight loss due to immune stimulation (e.g., endotoxin exposure) and the adverse effects of catabolic hormones (e.g., IL-1) was disclosed in U.S. Pat No. 5,430,066 (Cook, et al.), herein incorporated by reference. Chicks fed a diet of 0.5% CLA and subsequently challenged by endotoxin injection exhibited weight gain while chicks fed a control diet failed to gain weight following endotoxin exposure. Similar results were obtained in rats fed a diet containing 0.5% CLA as compared to animals fed a control diet of 05% corn oil. Preparations and dosage ranges disclosed were identical to those disclosed in U.S. Pat. No. 5,554,646.

Methods of treating animals to maintain or elevate CD-4 and CD-8 cell levels and to prevent or alleviate the adverse effects on the animal caused by the production or exogenous administration of tumor necrosis factor (TNF) or by a virus consisting of administering to the animal a safe and effective amount of CLA were disclosed in U.S. Pat. No. 5,674,901 (Cook et al.), herein incorporated by reference. Mice were fed either a control diet or 0.5% CLA and subsequently challenged with injections of TNF. Mice fed CLA lost less weight than the control mice. Likewise, chicks fed a 0.5% CLA diet and subsequently challenged with a wing web injection of live attenuated fowl pox virus gained more weight than chicks fed a control diet. Chicks fed the 0.5% CLA diet demonstrated a markedly enhanced percent of CD-4 and CD-8 cells as compared to chicks fed a control diet.

European Patent Application 779,033 A1 (Lievense, et al.), herein incorporated by reference, discloses the use of CLA for improving blood lipid profile. Briefly, hamsters were fed diets containing CLA incorporated into a triglyceride in the form of a fat spread at a rate of 1.5% of the total calories of their diet. Hamsters fed CLA exhibited a decrease in total cholesterol, a decrease in HDL cholesterol, and decrease in LDL cholesterol.

CLA has also been demonstrated to affect bone deposition, as reported in PCT Publications WO 98/05318 (Cook, et al.), and WO 98/05319 (Cook, et al.), both incorporated herein by reference. Chicks fed a diet containing 0.1875%, 0.375%, or 0.75% of the diet, exhibited a substantial decrease in skeletal abnormalities as compared to chicks receiving no CLA in their diet. Furthermore, chicks fed a diet containing 0.5% CLA exhibited on increase in bone mineral content.

Other patents describe various formulations of CLA. European Patent Application EP779033 A1 discloses an edible fat spread containing 0.05 to 20% (by weight) conjugated linoleic acid residues. There, a commercially-available mixture of free fatty acids having a linoleic acid content of 95.3% was subjected to alkali isomerization with NaOH in ethylene glycol. The free fatty acids were incorporated into triglycerides by mixing with 10 parts palm oil and lipase. The mixture was stirred for 48 hours at 45° C. and the lipase and free fatty acids removed. Seventy parts of this composition and 29 parts water, 0.5 parts whey protein powder, 0.1 parts salt, and a small amount of flavor and citric acid (to obtain a pH of 4.5) were combined and processed to produce a fat spread.

Other dietetic foods containing a safe and effective amount of CLA are disclosed in PCT Publication WO 97/46118 (Cook, et al.), herein incorporated by reference. There, a liquid dietetic food for parenteral administration to humans containing emulsified fat particles of about 0.33–0.5 micrometers in diameter is disclosed. The emulsion contains 0.5 mg/gm to 10 mg/gm of CLA or alternatively, 0.3% to 100% CLA based on the food lipid or 0.03 gm to 0.3 gm CLA per 100 calorie serving. This application also discloses a baby formula containing similar amounts of CLA along with 2.66 gm of protein, 5.46 gm of fat, 10.1 gm of carbohydrate, 133 gm of water, and vitamins and minerals in RDA amounts. Another example of a low-residue liquid enteral dietetic product useful as a high-protein, vitamin and mineral supplement is disclosed. This supplement contains CLA at 0.05% to about 5% by weight of the product, or by 0.3% to about 100% of the lipid present or about 0.03 to 0.3 gm CLA per 100 calories. Additionally, 140 calories of a representative formula can contain 7.5 gm of egg white solids, 0.1 gm CLA, 27.3 gm carbohydrate such as sucrose or hydrolyzed cornstarch, 1.9 gm of water, and vitamins and minerals in RDA amounts.

In the present invention, preparations enriched for either the 10,12 isomer or 9,11 isomers are preferably utilized for each of the applications described above. Enriched preparations of the 9,11 isomer are available commercially from Matreya (State College, Pa.). CLA preparations enriched for the t10,c12 isomer may preferably be prepared by preparative scale gas chromatography, as is known in the art.

The Inventors have discovered, contrary to most current scientific opinion, that a particularly active CLA isomer may actually be the t10,c12 isomer of CLA. In the present invention, the ratio of 10,12 to 9,11 isomers, most preferably the ratio of t10,c12 to c9,t11 isomers, added to human food supplements and animal feeds is controlled to provide desirable nutritional, therapeutic and pharmacologic effects. The ratio of 10,12 to 9,11 isomers, most preferably the ratio of the t10,c12 to c9,t11 isomers, utilized is about greater than 1.2:1, most preferably between about 1.2:1 to 3:1. Because CLA is non-toxic, the upper limit of the ratio of the 10,12 to 9,11 isomers is not important. However, it is expected that exceeding the 3:1 ratio threshold will result in relatively minor additional benefit; however, delivery of enriched 10,12 CLA will be efficacious at levels that exceed its maximum observed effect.

The compositions of the present invention are preferably formulated by combining an enriched preparation of the t10,c12 isomer with either an enriched preparation of the 9,11 isomer or a normal CLA preparation produced by alkali isomerization. In each case, the enriched preparation of the 10,12 isomers is added so that the desired ratio of 10,12 to 9,11 isomers is achieved. The isomer composition of the various CLA preparations may preferably be confirmed by gas chromatography, as is known in the art.

Alternatively, the 10,12 isomers may be provided as a daily ration in a vehicle with a lipid component containing or comprising 0.01 to 10 gram equivalents of the 10,12 isomers, most preferably 0.01 to 10 gram equivalents of the t10,c12 isomer. Gram equivalents means that the total amount of 10,12 isomers provided, irrespective of other isomers present, is from 0.01 to 10 grams. The amount of 10,12 isomer present may be that amount which results in a 10,12 to 9,11 ratio of about greater than 1.2:1. When the 10,12 isomers are provided as part of a daily ration, the intake may occur in a single dose, or as a series of doses in a feed or various food products consumed throughout the day.

The compositions of the present invention may also take the form of a bulk product for sale in commerce. The bulk CLA product contains or comprises at least 50 percent conjugated linoleic acid isomers. The linoleic acid isomers may be characterized in containing greater than 90 percent of a mixture of t10,c12 and c9,t11 isomers. Preferably these isomers are provided in a ratio of greater than about 1.2:1 in favor of t10,c12, most preferably in a range of about 1.2:1 to 3:1. This bulk product may be diluted into nutritional products such as animal feeds, human dietary supplements, and human food products. Those products will be compositions containing or comprising linoleic acid isomers characterized in containing greater than 90 percent of a mixture of t10,c12 and c9,t11 isomers. Preferably these isomers are provided in a ratio of greater than about 1.2:1 in favor of t10,c12, most preferably in a range of about 1.2:1 to 3:1.

The compositions of the present invention will have a variety of uses. These uses include: the reduction of body fat in animals; increasing muscle mass in animals; increasing feed efficiency in animals, reducing body weight in humans, attenuating allergic reactions in animals; preventing weight loss due to immune stimulation in animals; elevating CD-4 and CD-8 cell counts in animals; increasing the mineral content of bone in animals; preventing skeletal abnormalities in animals; and, decreasing the amount of cholesterol in the blood of animals. In each case, the term animal includes all mammals including humans. The preferred dosages and ratios of the 10,12 isomers, most preferably the t10,c12 isomer, utilized for each application are the same as described above.

Derivatives of the 10,12 and 9,11 isomers may also be utilized in the present invention. The CLA may be free or bound through ester linkages. For example, the CLA may be provided in the form of an oil containing CLA triglycerides. The triglycerides may be partially or wholly comprised of CLA attached to a glycerol backbone. Furthermore, the CLA may be in the form of a non-toxic salt, such as a potassium or sodium salt, which is formed by reacting chemically equivalent amounts of the free acids with an alkali hydroxide at a pH of about 8 to 9. The CLA may also be used in liquid, gel or powdered forms.

The preferred method of administration is oral. The CLA may be formulated with suitable carriers such as starch, sucrose or lactose in tablets, capsules, solutions and emulsions. The tablet or capsule of the present invention may be coated with an enteric coating which dissolves at a pH of about 6.0 to 7.0. A suitable enteric coating which dissolves in the small intestine but not in the stomach is cellulose acetate phthalate.

The CLA preparations may also be provided as supplements in various prepared food products For the purposes of this application, prepared food product means any natural, processed, diet or non-diet food product to which CLA has been added The CLA may be added in the form of free fatty acids or as an oil containing partial or whole triglycerides of CLA. Therefore, CLA may be directly incorporated into many prepared diet food products, including, but not limited to diet drinks, diet bars and prepared frozen meals.

Furthermore, CLA may be incorporated into many prepared non-diet products, including, but not limited to candy, snack products such as chips, prepared meat products, milk, cheese, yogurt and any other fat or oil containing foods.

CLA is also susceptible to oxidation. Therefore it is desirable to package CLA for human use with suitable antioxidants such as lecithin, tocopherols, ascorbate, ascorbyl palmitate or spice extracts such as rosemary extract.

Currently, most CLA is manufactured by the alkali isomerization process. An oil containing a high amount of linoleic acid such as sunflower oil, evening primrose oil or safflower oil is reacted in an inert nitrogen environment with potassium hydroxide and a solvent such as ethylene glycol at about 180° C. for about 2.5 hours. The reaction product is acidified and extracted with hexane, and the hexane removed by vacuum. For a complete description of the production of CLA by alkali isomerization, see U.S. Pat. No. 5,554,646, incorporated herein by reference. Most preferably, the CLA may be produced by the continuous flow alkali isomerization process described in U.S. Pat. No. 4,164,505, incorporated herein by reference. The reaction product obtained from these processes is a mixture of CLA, linoleic acid and the other fatty acids found in the source oil Generally, the amount of CLA derived from alkali isomerization of sunflower oil is about 60% of the total free fatty acid product Another method of producing a preparation consisting of primarily cis-9, trans-11 CLA is disclosed in U.S. Pat. No. 5,674,901, incorporated herein by reference In that method, linoleic acid containing oil is incubated with the microorganism *Butyrivibrio fibrisolvens*. *B. fibrisolvens* contains an $\Delta^{12}$-cis,$\Delta^{11}$-isomerase which converts linoleic acid into cis-9, trans-11 CLA.

EXAMPLES

Example 1

Three different studies have been conducted which examine the relationship between CLA content in feed and the amount of back fat in hogs In a study conducted at Iowa State University and reported at the Midwest Animal Science meetings, R. L. Thiel et al reported that pigs fed CLA experience a reduction in back fat. Briefly, eight replications of five littermate barrows with an average initial weight of 26.3 kg were allotted randomly to individual pens. The pigs were fed for an average of 93 days and had an average weight of 116 kg at slaughter. The group fed a diet of 0.5% CLA experienced a 10.3% decrease in back fat. Although not initially published, the CLA utilized in the diets contained a ratio of 10,12 to 9,11 isomers of CLA of 1.05:1

In another study conducted by researchers at Kansas State University and reported at the Midwest Animal Science Meetings, 36 crossbred barrows with an average initial weight of 83 lbs. were fed a diet containing 0.50% CLA. The average ending weight was approximately 230 lbs. The barrows fed diets containing CLA experienced a 7.2% decrease in back fat. The ratio of 10,12 to 9,11 isomers of CLA in the CLA utilized in this experiment was 0.487:1.

In another study, as yet unpublished, 24 barrows with a beginning weight of 26 kg were fed a diet containing 0.48% CLA or a control diet. The hogs were fed to an ending weight of 118 kg. Hogs fed CLA experienced a 13.7% decrease in back fat. The ratio of 10,12 to 9,11 isomers of CLA in this experiment was 1.16:1.

The ratio of 10,12 to 9,11 isomers of CLA utilized in each of these studies was plotted against percent reduction back fat and analyzed by logarithmic regression. The results are presented in FIG. 1. These results indicate that as the ratio of 10,12 to 9,11 isomers of CIA increases, the percent reduction in back fat also increases. Therefore, preparations of CLA containing a ratio of 10,12 to 9,11 of greater than about 1.2:1 are desirable.

The total amount of 10,12 isomers in the diet may also effect backfat deposition. The percent of 10,12 isomers in the diets was plotted against percent reduction backfat and analyzed by linear regression. The results are presented in FIG. 2. These results demonstrate that as the total amount of 10,12 isomers in the diet increases, backfat is reduced. The effect seen is not as great as for isomer ratio. However, these results may be consistent with the ratio results. The studies relied upon did not differentiate between isomers. It is possible that the amounts and ratios of the 9,11 and other isomers present masked any effect relating to the increasing percentage of 10,12 in the diet. When a preparation of CLA enriched for the 10,12 isomer is utilized, it is expected that the results will be comparable to the ratio results.

Example 2

The scientific literature indicates that either the biologically active isomers of CLA have not been identified, or that c9,t11 CLA is the biologically active isomer. Based on the results of Example 1, the Inventors believe that the t10,c12 isomer is the active isomer. Therefore, the effect of feeding different ratios and amounts of CLA isomers to mice is examined to demonstrate that the t10,c12 isomer is the biologically active isomer and that the ratio of t10,c12 to c9,t11 may be manipulated to produce desirable biological effects. Briefly, a total of 78 mice are divided into a total of 13 treatment groups with 2 pens per treatment, 3 mice per pen. Each treatment is assigned to pens using a randomized block design and mice randomly assigned to pens. Different treatment groups are fed either a normal diet or feed containing varying amounts and ratios of preparations of CLA enriched for t10,c12 and c9,t11 isomers. The total duration of the treatment is three weeks. The treatment groups are as follows:

| Treatment | 10, 12* | 9, 11* |
|---|---|---|
| 1 | 0 | 0 |
| 2 | 0.1% | 0 |
| 3 | 0 | 0.1% |
| 4 | 0.2% | 0 |
| 5 | 0.4% | 0 |
| 6 | 0 | 0.2% |
| 7 | 0 | 0.4% |
| 8 | 0.1% | 0.2% |
| 9 | 0.2% | 0.1% |
| 10 | 0.4% | 0.2% |
| 11 | 0.2% | 0.4% |
| 12 | 0.2% | 0.2% |
| 13 | 0.4% | 0.4% |

*% of isomer in diet, based on total calories.

Prior to the initiation of the trial, mice are acclimated for a period of two days. The mice are selected on the basis of comparable size and general good health at two days post-acclamation. Mice which show definite signs of illness or abnormalities are eliminated from the study. Treatments are assigned by random block design. Body weight will be recorded weekly. Each mouse is analyzed for total body fat by ether extraction at the end of the study. Final data is expressed as the average gain and final body weight for each treatment group as well as total body fat. Statistical analysis is performed by ANOVA utilizing SAS.

The results will show that as the total amount of t10,c12 CLA and the total ratio of t10,c12 to c9,t11 isomers of CLA increases, percent body fat will decrease and rate of gain will increase as compared to the control diet.

Example 3

A preparation of CLA enriched for the 10,12 isomer was prepared by preparative scale gas chromatography. The resulting product was analyzed by gas chromatography. For recent descriptions of gas chromatography methods for identifying CLA isomers, see Christie et al., *JAOCS* 74(11) :1231 (1997), Christie et al., *Lipids* 33 (2): 217–21 (1998), Sehat et al., Lipids 33(2):217–21 (1998), and Marcel S. F. Lie Ken Jie and J. Mustafa, *Lipids* 32 (10): 1019–34 (1997). The foregoing references are herein incorporated by reference. The gas chromatography conditions were as follows:

| | |
|---|---|
| System: | Perkin-Elmer Auto System |
| Injector: | Splitless at 240° C. |
| Detector: | Flame Ionization Detector at 280° C. |
| Carrier: | Helium |
| Column: | WCOT Fused Silica 0.25 mm × 100 M, CP-SL 88 for FAME, DF 0.2 |
| Oven Program: | 80° C. (0 min.) increasing to 220° C. at 10° C. per min. and held at 220° C. for 10 min. |

All results are expressed as the relative peak area percentage. The results of the analysis were:

| Isomer | Area (%) |
|---|---|
| C16:0 | 2.01 |
| C18:0 | 0.57 |
| C18:1 | 0.26 |
| c9, t11 | 1.61 |
| t10, c12 | 92.75 |
| t9, t11; t10, t12 | 1.16 |
| Unidentified | 1.64 |
| Total | 100.0 |

What is claimed is:

1. A composition comprising an excipient and a conjugated linoleic acid component, said conjugated linoleic acid component comprising greater than about 75% of the c9,t11 isomer of conjugated linoleic acid.

2. The composition of claim 1, wherein said c9,t11 isomer is provided as an ester.

3. The composition of claim 1, wherein said c9,t11 isomer is provided a triglyceride.

4. The composition of claim 1, wherein said excipient is selected from the group consisting of starch, sucrose, and lactose.

5. The composition of claim 1, further comprising about 0.01 to 10 gram equivalents of said c9,t11 isomer of conjugated linoleic acid.

6. A composition comprising a capsule, said capsule containing a conjugated linoleic acid component comprising greater than about 75% of the c9,t11 isomer of conjugated linoleic acid.

7. The composition of claim 6, wherein said c9,t11 isomer is provided as an ester.

8. The composition of claim 6, wherein said c9,t11 isomer provided as a triglyceride.

9. The composition of claim 6, wherein said capsule has an enteric coating.

* * * * *